United States Patent [19]

Engelstad et al.

[11] Patent Number: 4,972,837
[45] Date of Patent: Nov. 27, 1990

[54] CONTRAST AGENTS FOR NUCLEAR MAGNETIC RESONANCE IMAGING

[75] Inventors: Barry L. Engelstad, Orinda; Robert C. Brasch; Robert S. Hattner, both of Mill Valley; George Wesbey, Sausalito; John P. Huberty, Corte Madera, all of Calif.

[73] Assignee: Regents of the University of California, Oakland, Calif.

[21] Appl. No.: 98,749

[22] Filed: Sep. 16, 1987

Related U.S. Application Data

[63] Continuation of Ser. No. 488,733, Apr. 26, 1983, abandoned.

[51] Int. Cl.$^5$ .................................................. A61B 6/00
[52] U.S. Cl. .................................. 120/654; 120/653 A
[58] Field of Search ........................... 128/654, 653 A; 436/173; 424/9; 435/4, 78; 536/56

[56] References Cited

U.S. PATENT DOCUMENTS

| 3,887,375 | 6/1975 | Newnan et al. | 430/483 |
| 4,269,850 | 5/1981 | Rogers | 562/444 |
| 4,352,751 | 10/1982 | Weider et al. | 435/4 |
| 4,359,477 | 11/1982 | Rogers | 514/492 |
| 4,448,763 | 5/1984 | Triplett | 128/659 |
| 4,454,106 | 6/1984 | Gansow et al. | 128/659 |
| 4,637,929 | 1/1987 | Quay | 128/654 |
| 4,656,026 | 4/1987 | Coffman et al. | 429/9 |

FOREIGN PATENT DOCUMENTS 8633082  1/1983  Australia .

OTHER PUBLICATIONS

The Merck Index, p. 412, No. 2839, 10th Edition, 1983.
"NMR Imaging in Medicine", Pykett, I., Scientific Am. vol. 246, No. 5, May 1982, pp. 78–88.

Primary Examiner—C. Fred Rosenbaum
Assistant Examiner—Kathleen A. Daley
Attorney, Agent, or Firm—Flehr, Hohbach, Test, Albritton & Herbert

[57] ABSTRACT

A method is provided for obtaining in vivo differentiation of tissues in an animal by nuclear magnetic resonance imaging comprising the steps of introducing into the animal a complex comprising a paramagnetic metal ion and a chelator.

5 Claims, 1 Drawing Sheet

CONTRAST AGENTS FOR NUCLEAR MAGNETIC RESONANCE IMAGING

This is a continuation of application Ser. No. 488,733 filed Apr. 26, 1983 now abandoned.

The present invention is directed to a method of in vivo non-invasive diagnostic imaging by the technique of NMR imaging utilizing chelated paramagnetic metal ions as contrast agents. The present invention is further directed to novel chelated paramagnetic metal ions which are useful as NMR imaging contrast agents.

The non-invasive in vivo diagnostic technique of NMR imaging has been utilized to produce cross-sectional images of living subjects without exposure to harmful ionizing radiation, as described, for example, by Hansen et al *Radiology*, 136: 695–700 (1980). An NMR imaging apparatus has been developed wherein cross-sectional NMR images of selected regions and various tissues within a living animal may be taken, as described by Crooks et al, *Radiology*, 136: 701–706 (1980).

An important principle of NMR imaging is that the spin-lattice (T1) and spin-spin (T2) magnetic relaxation times of various tissues often inherently differ. The values of T1 and T2 are the exponential time constants describing the rates with which hydrogen nuclei within a static magnetic field equilibrate. These rate constants depend on the physical environment, such as, temperature, viscosity, the external magnetic field strength and internal magnetic forces. Among the stable nuclei, hydrogen, which is the most abundant nucleus in the body, is the most useful for NMR imaging.

An important aspect of NMR imaging is its non-hazardous nature. The clinically used magnetic field strength and radio frequency levels of NMR produce no known physiological danger. See Budinger, *IEEE Trans. Nucl. Sci.* NS-26: 2821–2825 (1979). However, a limitation of NMR imaging is that only a fixed unit of contrast differentiation between certain pathologic and normal anatomic tissues may be obtainable. Thus, a means for increasing the NMR signal from selected tissues and organs is desirable to improve the observed contrast from surrounding tissues and organs. Therefore, there is a need for contrast agents in NMR imaging which increase the inherent contrast (i.e., difference in density) between different tissues or different regions of the same tissue as recorded by the imaging system. Such contrast agents as stable-free nitroxide radicals and manganese ion, have been used due to their paramagnetic nature. The effect of administered paramagnetic ions is chiefly to shorten both T1 and T2. The effect is concentration-dependent and generally follows the pattern following when the concentration of the paramagnetic ions increases: intensity initially increases due to the predominant effect of T1 shortening. At higher concentrations of the paramagnetic ions, intensity decreases due to the predominant effect of T2 shortening. However, in the continuing search for NMR imaging contrast agents, there is a difficulty in devising contrast agents which also meet other physiological criteria, such as being non-toxic to the animal and being excretable from the body.

It is, therefore, an object of the present invention to provide an improved method for in vivo NMR imaging utilizing paramagnetic chelated metal ions as contrast agents.

It is a further object of the present invention to provide novel chelated paramagnetic metal ions useful as contrast agents for in vivo NMR imaging.

It is another object of the present invention to provide non-toxic, excretable paramagnetic NMR imaging contrast agents.

These and other objects will be readily apparent to those of ordinary skill in the art from the following description and claims.

Figure 1:
FIG. 1 is an NMR image of the urinary collecting system of a rat enhanced by a contrast agent according to the present invention.

The present invention is directed to a method for increasing the emitted signal, and thus obtaining in vivo differentiation of tissues, in an organism by NMR imaging, by administering as a contrast medium a chelated paramagnetic metal ion. In particular, the paramagnetic metal ion may be selected from the paramagnetic electronic forms of iron, vanadium, copper, gadolinium, dysprosium, holmium, europium, cobalt, nickel, gallium and indium. The chelator for these paramagnetic metal ions may be organic chelating agents which are excretable by mammals. Particularly preferred chelators are desferrioxamine, diethylenetriaminepentaacetic acid, glucoheptonic acid and phytate.

A preferred class of chelated paramagnetic metal ions according to the present inventions includes the metal ions iron (III), vanadium (II), copper (II), gadolinium (III), dysprosium (III), holmium (III) and europium (III) chelated with one of the following chelators: desferrioxamine (hereinafter DF), diethylenetriaminepentaacetic acid (hereinafter DTPA), glucoheptonic acid (hereinafter GH) and phytate (inositol hexphosphate, hereinafter P).

A preferred chelated metal ion is iron (III) chelated with desferrioxamine (DF), which forms a complex known as ferrioxamine B, having the following structure:

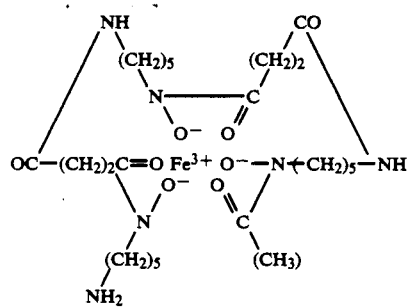

A particular advantage of ferrioxamine B is that the chelator, desferrioxamine B, is approved for use in humans in the form of desferrioxamine mesylate, and is commercially available. Desferrioxamine B is a known pharmaceutical for treatment of acute and chronic overload states and as a diagnostic agent for testing the severity of iron overload states. Desferrioxamine B is also excretable and has minimal toxicity to animals and humans.

A particularly advantageous feature of ferrioxamine B is that NMR contrast enhancement is achieved at doses lower than known NMR contrast agents. Typically, NMR contrast agents, such as nitroxide free radicals, are utilized in dosages of 100 mg contrast agent per 100 gm weight of the animal. However, use of ferrioxamine B achieves contrast enhancement at does as low as 1 mg contrast agent per kilogram weight of the animal.

While ferrioxamine B is a known compound, other chelated paramagnetic ions according to the present invention which are useful as NMR contrasting agents include novel iron (III) complexes with DTPA and GH, and vanadium (II), copper (II), gadolinium (III), dysprosium (III), holmium (III) and europium (III) ions complexed with DF, DTPA, GH or P. Conventional pharmaceutically acceptable derivatives of the chelators may also be utilized, such as the hydrates, salts and N or O-acylated derivatives. In particular, derivatives of desferrioxamine such as the monohydrate, hydrochloride, methanesulfonate and N-acetyl may be utilized.

The formation of the chelated paramagnetic metal ions is generally known. For example, stoichiometric amounts of the metal ion and the chelator may be admixed in a solution with an appropriate adjustment of pH, if necessary. The chelated metal ion may be isolated by conventional methods such as crystallization, chromatography, and the like, and admixed with conventional pharmaceutical carriers suitable for pharmaceutical administration.

The contrast agents according to the present invention may be used for imaging the circulatory system, the genitourinary system, hepatobiliary system and central nervous system, or for imaging tumors and abscesses in general. Contrast agents according to the present invention may also be useful to improve lesion detectability by NMR enhancement of either the lesion or adjacent normal structures.

The chelated metal ions may also be used in a conjugated form, i.e., conjugated with biomolecule. For example, the chelated paramagnetic metal ions may be conjugated to proteins such as tumor-specific monoclonal antibodies or to proteins such as albumin. Examples of such conjugated complexes may be gadolinium (III)-glucoheptonic acid albumin aggregate.

The contrast agents according to the present invention may be administered by any suitable method for introducing the contrast agent to the tissue area of interest. Preferably, the contrast agent may be introduced intravenously whereby dosages as low as 1 mg per kilogram weight of the animal are suitable to achieve contrast enhancements of the NMR image.

Exemplary chelated metal ions and conjugates thereof include the following: Fe (III)-DF, Fe (III)-DTPA, Fe (III)-GH, V (II)-DF, V (II)-DTPA, V (II)-GH, V (II)-P colloid, Cu (II)-DF, Cu (II)-GH, Gd (III)-DF, Gd (III)-DTPA, Gd (III)-GH, Gd (III)-GH albumin aggregate, Gd (III)-P colloid, Dy (III)-DF, Dy (III)-DTPA, Ho (III)-DF, Ho (III)-DTPA, Eu (III)-DF and Eu (III)-DTPA.

EXAMPLE 1

Samples containing 0.01 mM, 0.1 mM and 1.0 mM ferrioxamine B were prepared in vitro suspensions containing 0.9% NaCl. Samples containing 0.01 mM, 0.1 mM and 1.0 mM ferric chloride in vitro were also prepared. As a standard a 10 mM in vitro suspension of TES (N-succinyl-4-amino-2,2,6,6-tetramethyl-piperidino-1-oxyl) was prepared. At 0.1 mM concentration the ferrioxamine B NMR signal in vitro is weaker than an equal concentration of ferric ion, but at 1.0 mM concentration the ferroxamine B NMR signal is stronger than an equal concentration of ferric ion.

EXAMPLE 2

Figure 2:
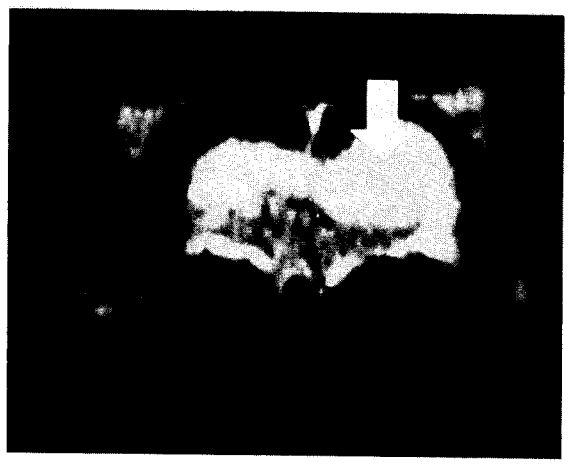
FIG. 2 shows an NMR image of the bladder of a rat enhanced by a contrast-aiding agent according to the present invention.

A solution of ferrioxamine B at physiologic pH and tonicity is injected into a rat at a dosage of 1 mg per kilogram body weight. The NMR image of the urinary collecting system (FIG. 1) and bladder (FIG. 2) of the rat show enhancement of urine which would normally appear black in absence of the contrast agent. The enhanced areas are shown by black arrows in FIGS. 1 and 2.

What is claimed is:

1. A method of obtaining in vivo differentiation of tissues in an animal by nuclear magnetic resonance imaging comprising the steps of introducing into said tissues a complex comprising a paramagnetic metal ion selected from the group consisting essentially of the paramagnetic electronic configurations of iron, vanadium, copper, gadolinium, dysprosium, holmium, europium, cobalt, and nickel, and a chelator selected from the group consisting essentially of desferrioxamine, diethylenetriaminepentaacetic acid, glucoheptonic acid and phytate, said complex being excretable by said animal, and observing a nuclear magnetic resonance image of said tissues.

2. A method according to claim 1 wherein said complex is conjugated with a biomolecule.

3. A method according to claim 1 wherein said complex comprises ferrioxamine B.

4. A method according to claim 3 wherein said ferrioxamine B is a ferrioxamine B derivative selected from a monohydrate, hydrochloride salt, methanesulfanate salt, or N-acetylated derivative.

5. A method according to claim 3 wherein said ferrioxamine B is conjugated with a biomolecule.

* * * * *